United States Patent [19]

Vito et al.

[11] Patent Number: 4,688,559

[45] Date of Patent: * Aug. 25, 1987

[54] ORTHOPEDIC LEG BRACE WITH CABLE CONTROL

[75] Inventors: Raymond P. Vito, Atlanta; H. Russell Boehm, Forest Park, both of Ga.

[73] Assignee: Georgia Tech Research Corporation, Atlanta, Ga.

[*] Notice: The portion of the term of this patent subsequent to Jul. 29, 2003 has been disclaimed.

[21] Appl. No.: 856,190

[22] Filed: Apr. 28, 1986

Related U.S. Application Data

[63] Continuation-in-part of Ser. No. 647,795, Sep. 6, 1984, Pat. No. 4,602,627.

[51] Int. Cl.⁴ .............................................. A61F 3/00
[52] U.S. Cl. ..................................... 128/80 F; 623/43
[58] Field of Search ............... 128/80 R, 80 C, 80 F, 128/88; 623/39, 43

[56] References Cited

U.S. PATENT DOCUMENTS 4,602,627  7/1986  Vito et al. ..................... 128/88 X Primary Examiner—Clifford D. Crowder
Attorney, Agent, or Firm—Newton, Hopkins & Ormsby

[57] ABSTRACT

The modular components of an orthopedic leg brace assembly are secured together around a flexible cable arrangement and the components are removable so that they may be dissambled for repair or for replacement with longer components to accommodate for a user's growth. The components inlcude an ankle-foot orthosis and upwardly extending side braces of stanchion form with an upper securing strap arrangement for securely surrounding a user's lower leg, a second pair of side braces of stanchion form with an upper securing strap arrangement for securely surrounding a user's thigh, and knee joint assemblies joining the ends of the braces to simulate the normal action of a user's knee during flexion and extension of the leg. The flexible cable arrangement allows the user to rigidly hold the entire unit in aligned, fixed relation when the leg is extended.

19 Claims, 23 Drawing Figures

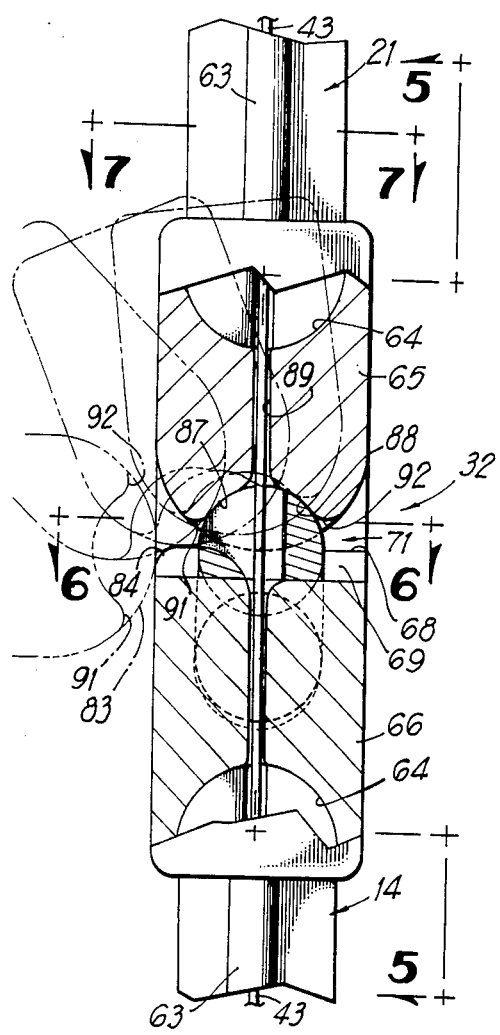
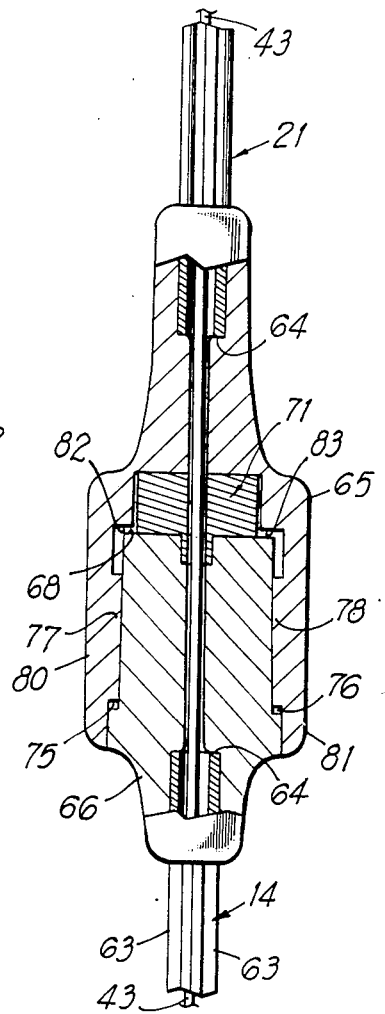
FIG 4  FIG 5
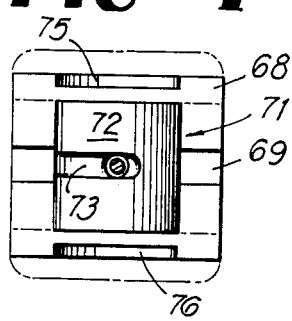
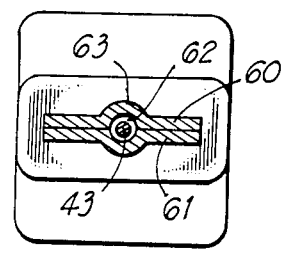
FIG 6  FIG 7

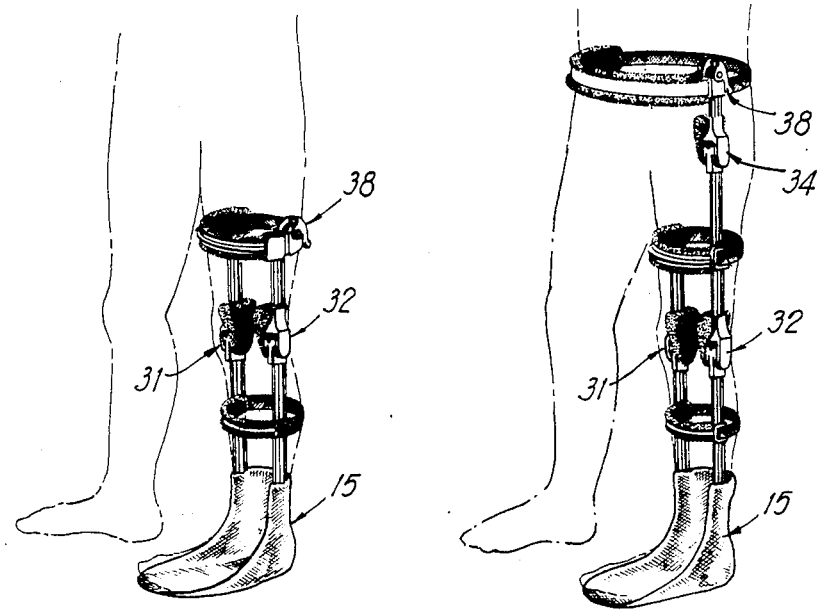
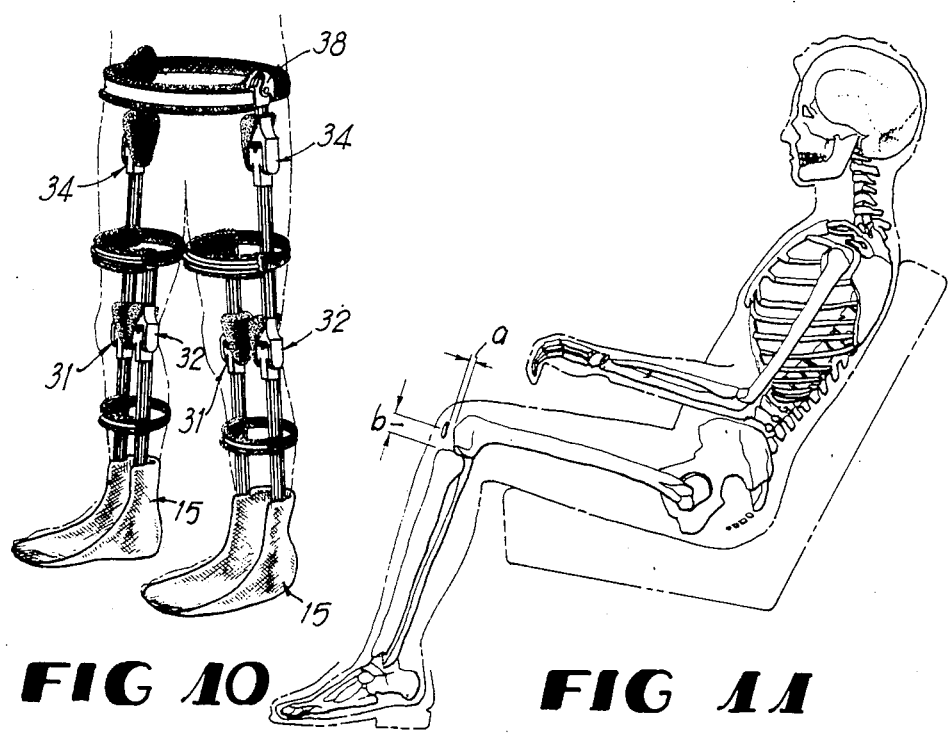
FIG 8  FIG 9
FIG 10  FIG 11

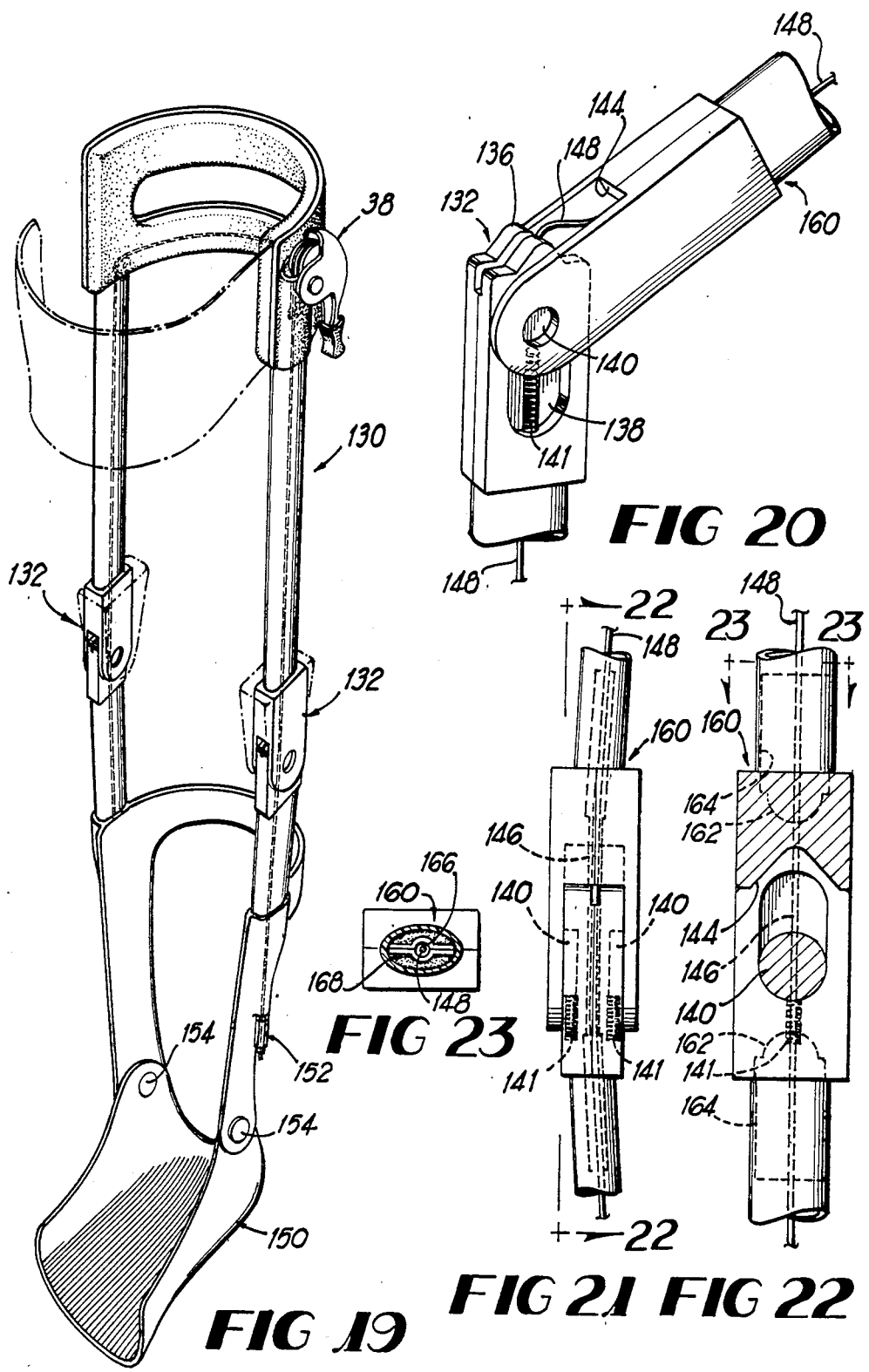

ORTHOPEDIC LEG BRACE WITH CABLE CONTROL

BACKGROUND OF THE INVENTION

This application is a continuation-in-part of co-pending application, Ser. No. 647,795 filed on Sept. 6, 1984, for an ORTHOPEDIC LEG BRACE, now U.S. Pat. No. 4,602,627.

The invention relates to orthopedic leg braces and especially those which brace the upper and lower portions of a user's leg and which incorporate a knee joint assembly. Attention is called to the following patents:
U.S. Pat. No. 4,361,142; 11/30/82; Lewis et al.
U.S. Pat. No. 4,289,122; 09/15/81; Mason et al.
U.S. Pat. No. 3,552,786; 05/12/69; Schmid It is well known, as is extensively discussed in the Lewis et al. patent, for example, that there is particular difficulty in providing knee orthoses which provide stability while duplicating or accommodating the complex actions of a normal knee during flexion and extension.

The long term need for one or both leg braces stems from temporary or permanent loss of neuro-muscular control or control of a knee or hip joint and it is particularly for such purposes that the invention is useful. For stability or bracing, the bracing is required to be secured firmly to the leg both below and above the knee and with the knee joint intervening between the bracings. If the knee joint is not effective to duplicate the compound, complex actions of a normal knee, not only is needless reaction imposed upon the user's knee during flexion and extension, but the tendency for relative movement between the firmly secured bracings and the user's leg is also a certainty. The former may well be injurious to the user and the latter results in proclivity to chafing, soreness or the like.

BRIEF SUMMARY OF THE INVENTION

It is, therefore, of concern to provide a knee orthosis which overcomes the above problems. At the same time, it is desired that the device be particularly suited for long term use and, to that end, it is of light weight and is simple to remove and replace by the user without the need for assistance. Moreover, the unit is modular so that it is easily modified from time-to-time to accommodate for the user's growth. At the same time, the device is not bulky and for that reason may be worn beneath normal clothing so as to be relatively unobtrusive. This is important particularly for children, although its benefit should not be disregarded for all classes of potential users.

Although the invention in its most fundamental form is especially applicable as a knee orthosis, the addition of upper thigh and hip bracings, united by a hip joint, is also within the scope of the invention.

Of basic concern is the utilization of upper and lower bracing elements, firmly secured to the user's leg respectively, above and below the knee, knee joint means being carried by the respective bracing elements and interengaged to duplicate or at least approximate the compound, complex actions of a normal knee, a flexible tension member, and means for variably altering the tension imparted to the tension member so that, with increased tension, the entire structure tends to become a rigid and aligned unit, particularly useful when the leg is extended. With the removal of the load, the cable can be released to easily flex the structure to duplicate or accommodate the compound, complex actions of a normal joint.

In a preferred embodiment, a pair of lower brace members are united to lie along the inner and outer sides of a user's leg and are provided with securing means for firmly anchoring them to the lower portion of a user's leg. A pair of upper brace members likewise are united and are provided with securing means for firmly anchoring them to the user's thigh. The upper and lower brace members have proximal ends which are joined by knee joint means which allow pivotal and sliding movement so that as a user's leg is flexed or extended, the normal action of a human knee is accommodated. A user actuated tensioning means is employed to guide elements of the knee joint means together so as to form a rigid brace between upper and lower members when the user's leg is extended. A locking device may additionally be provided, responsive to the tensioning means, to effect a positive locking action. In this preferred embodiment, part of the uniting means for the lower brace members may be in the form of an ankle-foot orthosis. The various members also have a unique connecting means therebetween which allow the present brace to be set up in such a manner as to accommodate the particular angles of the wearer's leg or legs to the extent of medically acceptable limits. This prevents any undue stress on the musculature or skeletal structure and allows the entire brace structure to be assembled without the use of fasteners such as screws, clamps, or the like.

The tensioning means includes a flexible member such as a cable which preferably acts to interconnect the elements and to aid in the operation of the knee joint means. This allows the brace assembly to be of very compact form so that it may be worn beneath a user's clothing, while at the same time permitting the novel knee movement simulation and rigid bracing action. It also allows the aforesaid ease of modification from time-to-time to accommodate for the user's growth, i.e., it is of modular form.

These and other objects of the invention will become apparent from the following description, with reference to the accompanying drawings.

BRIEF DESCRIPTION OF THE DRAWING FIGURES

FIG. 4 is a partial section of the knee joint illustrated in FIG. 3;

FIG. 5 is a partial section as indicated by section line 5—5 in FIG. 4;

FIG. 6 is a horizontal section as indicated by section line 6—6 in FIG. 4;

FIG. 7 is a horizontal section through one of the base members as indicated by section line 7—7 in FIG. 4;

FIG. 8 is a perspective view of another embodiment of the invention;

FIG. 9 is a perspective view similar to FIG. 1;

FIG. 10 is a perspective view of a further embodiment of the invention;

FIG. 11 is a diagrammatic view illustrating the need for sliding connection in the knee joint of the brace;

FIG. 19 is a perspective view of an embodiment having a modified knee joint means;

FIG. 20 is a partial perspective view showing the knee joint means of the previous figure in flexed position;

FIG. 21 is a partial, side elevational view, illustrating the adaptability of the present brace to an individual leg configuration;

FIG. 22 is a cross-sectional view illustrating the brace connecting means, the section being taken on line 22—22 of FIG. 21; and FIG. 23 is a cross-sectional view of the connecting means, the view being taken on line 23—23 of FIG. 22.

DETAILED DESCRIPTION OF THE INVENTION

Figure 1:
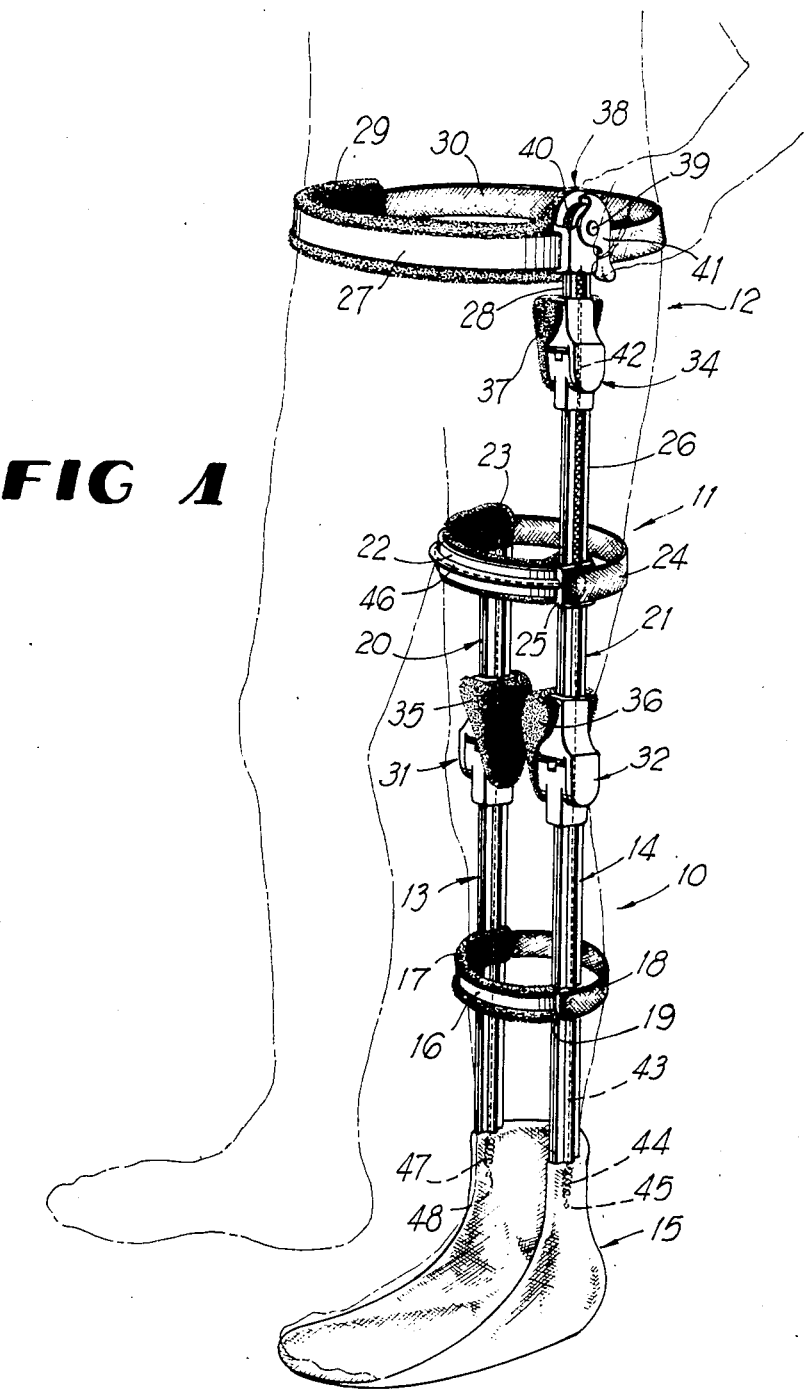
FIG. 1 is a perspective view of one embodiment of the invention.

With reference to FIG. 1, one form of the invention is illustrated therein and in this configuration it will be seen to include a lower leg assembly indicated generally by the reference character 10, an upper leg or thigh assembly indicated generally by the reference character 11, and a hip assembly indicated generally by the reference character 12. The lower assembly 10 comprises a pair of rigid, elongate side braces 13 and 14 which, in the embodiment shown, are associated with an ankle-foot orthosis indicated generally by the reference character 15. These two members 13 and 14 are rigidly interconnected by an arch-like brace or rigidifying member 16 provided with suitable padding material 17 which overlaps on the inner side of the members 13 and 14. There is provided a securing means in the form of a strap or straps 18 of flexible material, such as cloth or the like, having a Velcro fastening joint as indicated by the reference character 19, or with some other means for releasably joining the strap. The orthosis 15 has the lower ends of the members 13 and 14 secured thereto and thus functions, together with the member 16, to rigidly unite the brace members 13 and 14 so that they are disposed along inner and outer sides of the user's leg from the ankle and foot region to the region of the knee.

The upper assembly 11 includes the inner side member 20 and the outer side member 21 which are rigidly united by the arch-like member 22. Member 22 is provided, as is the case for the member 16, with the padding 23 overlapping the inner sides of the members 20 and 21 as shown. Also associated with these two members 20 and 21 is the securing means in the form of a flexible strap 24, also having a Velcro or similar fastener at 25. In this embodiment of the invention, the upper member 21 is extended, as indicated by the reference character 26, to terminate in the region of the user's hip joint. A waistband member comprising a rigid arch-like construction 27 carries a short brace element or member 28 and is also provided with interior padding as at 29 and has associated with it a flexible strap 30, also having a Velcro-type fastening. The upright brace members, the connecting arch-like members and the ankle-foot orthosis are normally constructed of a suitable, lightweight composite resin material. Graphite/fiber materials are especially suitable; however, similar lightweight plastics, thermoplastics or metals may be used.

As thus far described, it will be appreciated that the two members 13 and 14 which form the lower brace mechanism and the upper brace member 20 and 21 are more or less in axial alignment with each other when the user's leg is extended as is shown in FIG. 1 and the proximal ends of these members 13,20 and 14,21 are pivotally and slidably interconnected by the knee joint means indicated generally by the reference characters 31 and 32, the details of which will be presently described. Likewise, the extension 26 and the short brace member 28 are joined by a hip joint mechanism indicated generally by the reference character 34 which establishes a pivotal connection between these members, there being no necessity for the sliding connection which characterizes the knee joint means 31,32. It will be readily apparent that the orthopedic device shown in FIG. 1 may be easily removed and replaced by the user simply by disconnecting the straps 18, 24 and 30 or restrapping them in place. For added comfort, the knee joint means 31 and 32 have padding 35 and 36 associated therewith and the hip joint 34 likewise has padding 37, substantially as is shown.

In addition to the components generally described above, the rigid waistband 27 carries a pawl and ratchet type assembly or the like, indicated generally by the reference character 38, the pivotal axis of which is indicated at the reference character 39, for rotatably receiving the ratchet wheel 40 and the operating lever 41 thereof. The pawl (not shown) is accessible and releasable by the user, as is the lever 41. The purpose of this mechanism is to allow the user to manipulate the tensioning means which is a characteristic of this invention. In the embodiment shown, the tensioning means includes an upper flexible tension member or cable 42 and a lower flexible tension member or cable 43. One end of the cable 43 is connected to a tension spring 44 which is anchored at 45 to the lower end of the brace member 14 and the cable 43 extends upwardly within a channel of the member 14, through the knee joint means 32, through the upper member 21 and then in crossing over relation within the channel or bead 46 of the arch-like member 22 and thence downwardly within the member 20, through the knee joint means 31, and through the member 13 to connect to a further tension spring 47 which is anchored at 48 to the lower end of the member 13. The cable 42 is connected to the cable 43 by means of a suitable ring or loop so that when the pawl and ratchet mechanism 38 is operated to tension the cable against the springs 44 and 47, components of the several joints 31, 32 and 34 will be engaged so as to at least resist pivotal motions thereat and effectively function as a rigid orthopedic brace unit for the user's leg and hip in the particular embodiment shown. By releasing or relaxing the tension when weight is removed from the leg, the user may then allow normal pivotal motions of the knee joint means 31 and 32 and the hip joint 34 so as to allow easy motion of the hip joint as well as the knee joint.

Figure 17:
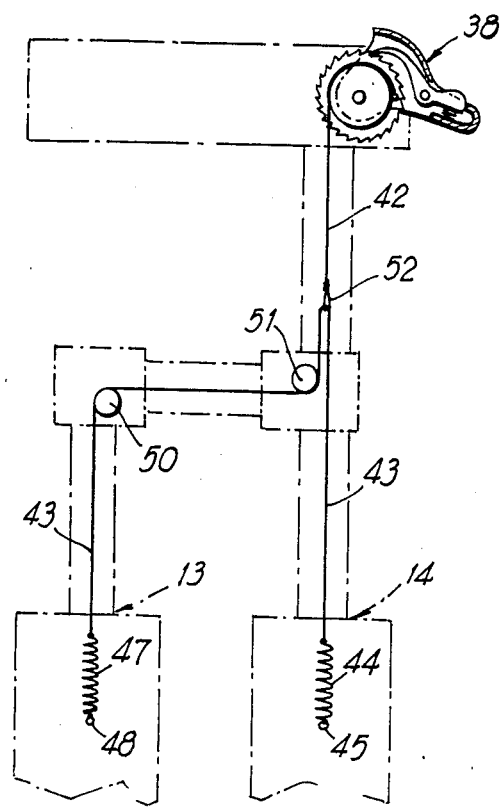
FIG. 17 is a diagrammatic view illustrating one form of tensioning means.

To facilitate an understanding of the cable arrangement shown in FIG. 1, reference is had to FIG. 17. From FIG. 17, it will be appreciated that at those points where the cable 43 must be directed substantially through right angles, suitable guide elements 50 and 51 may be employed. FIG. 17 also shows the ring or loop 52 which connects the upper cable 42 to the lower cable 43, the purpose of the loop or ring connection at 52 being to allow the cable 43 to be tensioned evenly throughout its length so as to impose the same interengaging action at both of the knee joint means 31 and 32.

Figure 18:
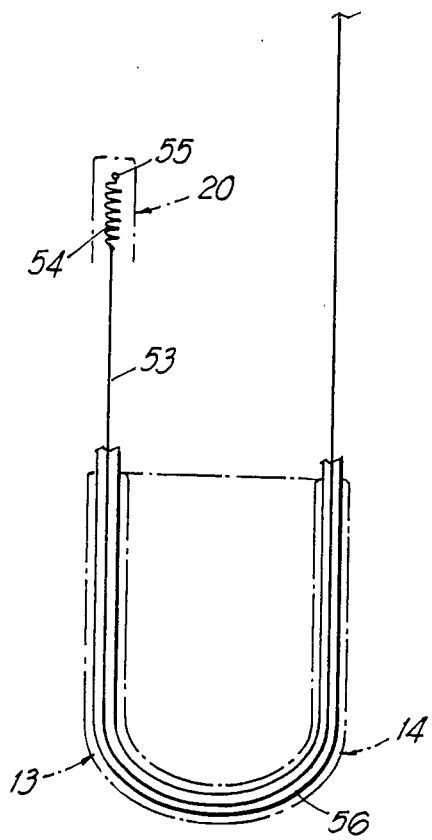
FIG. 18 is a diagrammatic view illustrating another form of tensioning means.

An alternative cable construction employing but a single cable is shown in FIG. 18. In this case, the single length of cable 53 is connected to one end of the tension spring 54, which is pin connected at 55 to the upper end of the member 20. The cable passes beneath the user's foot within the foot orthosis 15, through any suitable guiding mechanism 56, which may, if desired, be formed as extensions of the lower ends of the members 13 and 14, and thence upwardly for connecting ultimately to the pawl and ratchet mechanism which is not illustrated in FIG. 18.

Referring at this time more particularly to FIGS. 2-7, wherein one of the knee joint means is shown, it will be noted first of all from FIG. 7 that the brace members are formed as two halves in this embodiment, preferably from a fiber/resin composition or other lightweight materials, one of which is indicated by the reference character 60 and the other by the reference character 61. The side flanges of these halves are suitably secured together and it will be noted that their intermediate portions define a longitudinal channel 62 by virtue of the bead formations 63 formed on each half. These channels 62 receive the flexible tension member such as the cable 43, substantially as is shown.

As can be seen from FIGS. 4 and 5, the ends of the brace members are rounded as is indicated at reference characters 64 and the two main components 65 and 66 of the two knee joint assemblies 31,32 are recessed correspondingly to receive these ends in slip-fitted relationship therewith. This relationship is extremely useful when the orthopedic device is fitted to a growing person such as a child, inasmuch as it will be readily apparent that at time intervals, such as are indicated by growth, a new orthopedic device may be fabricated simply by replacing the various brace elements with slightly longer ones to accommodate for that growth.

Figures 2, 3:
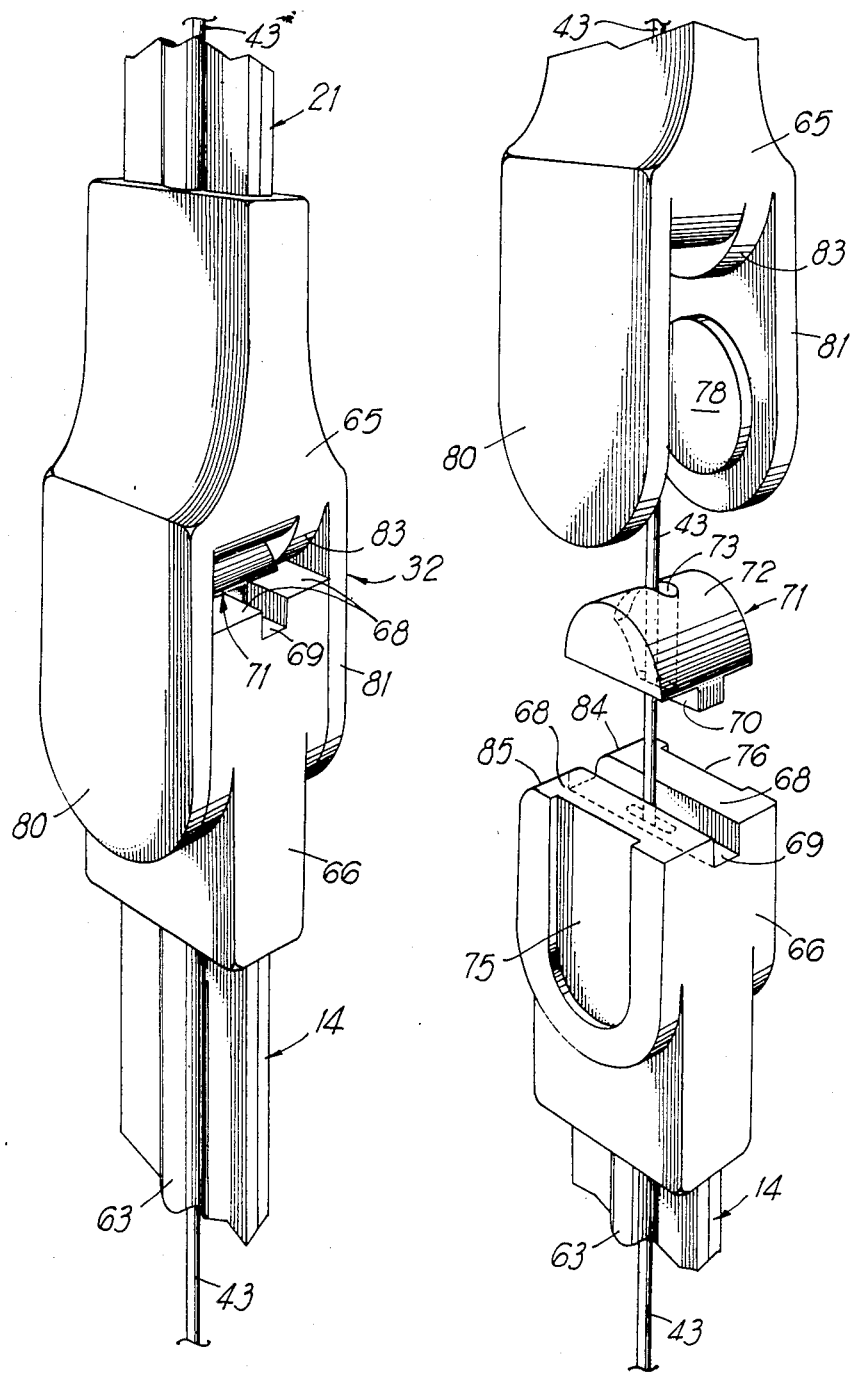
FIG. 2 is an enlarged perspective view of portions of upper and lower brace members connected by a knee joint.
FIG. 3 illustrates the components of FIG. 2 in exploded relation.

The construction of the knee joints 31 and 32 is illustrated in FIGS. 2 and 3. As is shown in FIG. 3, the lower element 66 is provided with a top flat surface 68 interrupted by the slot or channel 69, which slot is adapted to receive the tongue 70 of the semicylindrical member indicated generally by the reference character 71. The member 71 presents a semicylindrical surface 72 and is provided with a generally fan-shaped slot 73 which receives the cable 43 or its equivalent therethrough, substantially as is shown in FIG. 3. The member 71 is adhesively secured to the upper portion of the member 66 by suitable adhesive material such as synthetic resin, cured to effect the requisite bonding action of these two components.

The reason for the separate construction of the member 71 rather than integrally with the member 66 is to allow the cylindrical surface 72 to be positioned very accurately back and forth by sliding the tongue 70 in the groove 69 to fit the needs of an individual user. The opposite sides of the member 66 are provided with the side face recesses 75 and 76 which are adapted to receive the pivot bosses 77 and 78 (see also FIG. 5), which are mutually, oppositely directed toward one another on the inner side of the depending leg portions 80 and 81 of the upper member 65.

In addition to the bosses 77 and 78, the inner sides of the legs 80 and 81 are provided with cam surfaces 82 and 83, which are adapted to cooperate with the rounded cam corners 84 and 85 of the lower part 66, as will be more evident hereinafter when a further description of FIG. 4 is given. Between the cam surfaces 82 and 83, the juncture between the two legs 80 and 81 is formed as a saddle to present the arcuate surfaces 87 and 88 as shown in FIG. 4, which are adapted to seat upon the cylindrical surface 72 in full engagement therewith, insofar as the full extents of the surfaces 87 and 88 are concerned. The two surfaces 87 and 88 are disposed on either side of the central channel 89 which passes the tensioning member 43 therethrough. When, however, the upper portion 65 is rotated with respect to the lower portion 66, the rounded corners 91 and 92 of the saddles are effective to allow the camming action illustrated by the various dashed line positions of the upper member 65 shown in FIG. 4.

For example, the more the upper member 65 is rotated toward the right angular position with respect to the member 66, the rounded corner 92 becomes the only bearing point on the surface 72, the remainder of the saddle having been moved away. Ultimately, the cam surfaces 82 and 83 engage their respective corners 84 and 85. The purpose of this camming action is to cause a relative sliding movement between the upper and lower portions 65 and 66. Thus, the bosses 77 and 78 ride upwardly within their recesses 75 and 76. This action may be seen to correspond accurately with the normal action of the user's knee.

To illustrate this normal action, reference is had to FIG. 11 wherein the two distances a and b are shown. When the leg is flexed as shown in FIG. 11, the total distance a plus b has to be accommodated, the distance b being that to which the lower leg portion is extended relative to the upper leg portion. This is the extent to which the camming action must be applied to allow the lower brace members 13 and 14 to move away from, relatively, the upper brace members 20, 21. When the user is standing upright or when the leg is extended, the distance b as between the upper and lower brace members must be reduced. The camming mechanism may be accurately constructed to accommodate precisely for the distance b for a particular user. This will assure that there is absolutely no stress or strain applied to the user's knee joint by the present brace during flexion and extension of the leg, and that the firmly anchored upper and lower braces will not tend to ride or creep along the user's skin, such as might cause chafing or soreness.

On the other hand, it is not essential that the exact duplication of the knee action be attained, but that sufficient sliding action be achieved so as to alleviate any undue stress or strain. To aid in this application, it is appreciated that the springs, such as 47 and 44 or the spring 54 will, when the tensioning means is relaxed, still have sufficient tension to easily allow accommodations for variations in motions as between the knee joint means and the actual normal motion of the user's knee.

It will also be appreciated from FIG. 4 that when the knee joint component parts 65 and 66 are in the leg extended position as is shown in full lines in that Figure, an increased tension on the cable 43 will firmly interengage the component 71 in the arcuate saddle surfaces 87 and 88 of the upper member 66. This tends to rigidly unite the upper and lower brace portions so that the brace is stiffened, supporting the wearer despite the fact that significant muscle deterioration may be present in the leg musculature. When the user desires to flex the leg, the pawl and ratchet mechanism 38 is released to decrease the tension on the cable 43 and thus allow relatively easy sliding motion between the portions 65 and 66 for flexing the leg.

FIG. 9 shows the assembly of FIG. 1 whereas FIG. 8 shows a modified form of the invention wherein the hip joint and waist connector are not employed, the pawl and ratchet 38 then being located at the thigh connection as illustrated. Alternatively, a full orthopedic hip and knee brace for both legs may be utilized as is shown in FIG. 10, in which case there will be an individual pawl and ratchet 38 for each leg.

Insofar as the hip joints 34 of this invention are concerned, where used, they need not be of a sliding and pivoting type, but merely provide a pivoting action. Thus, they may be identically constructed as is shown in FIGS. 2-7 except for the camming surfaces mentioned in connection therewith.

Figures 12, 13:
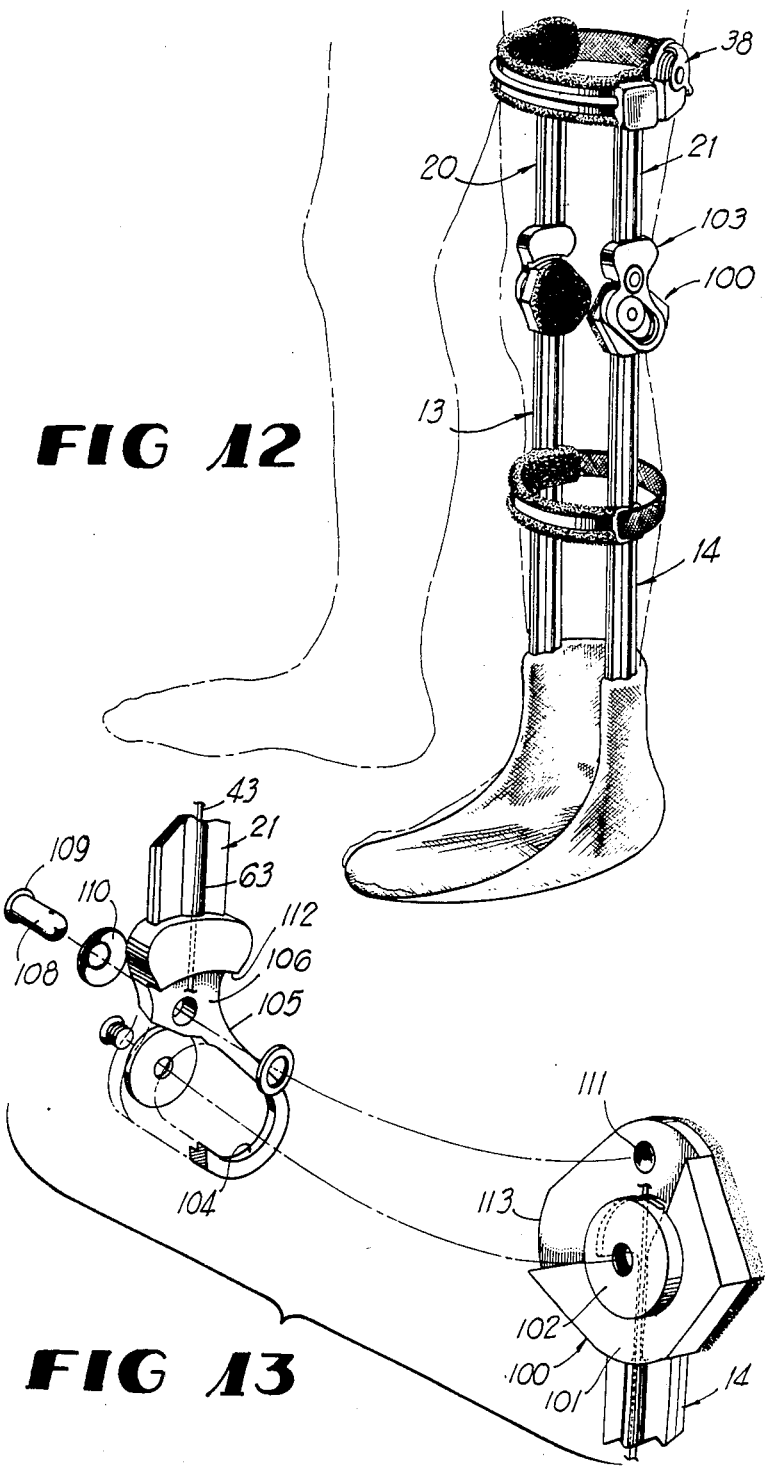
FIG. 12 is a perspective view of still another embodiment of the invention using a modified knee joint.
FIG. 13 is a exploded perspective view of the modified knee joint.
Figure 14:
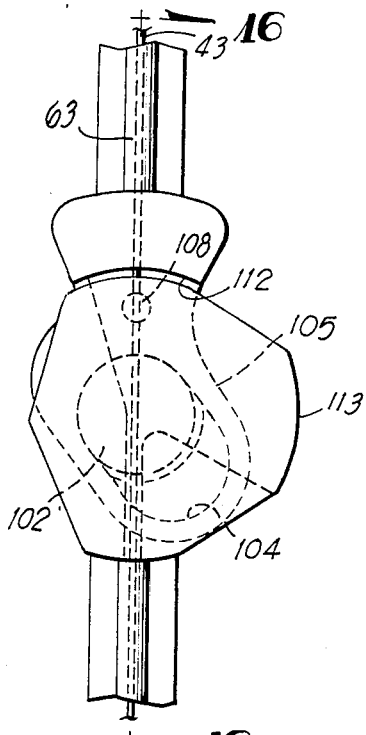
FIG. 14 is an elevation of upper and lower brace members connected by the modified knee joint.
Figure 16:
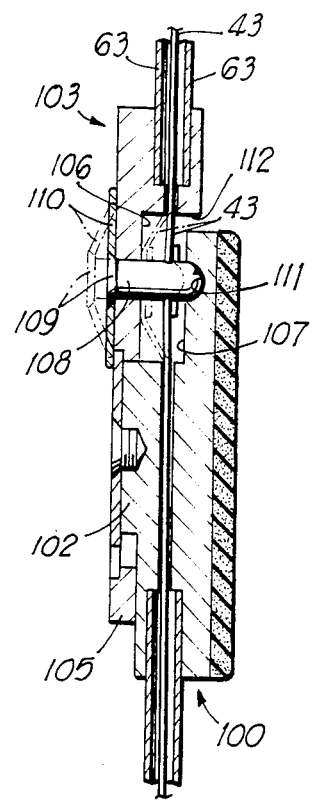
FIG. 16 is a vertical section taken along section line 16—16 in FIG. 15.

A modified form of knee joint means is illustrated in FIGS. 12 through 16. In this configuration, the lower member 100 of the knee joint means is provided on one side face 101 with an outstanding circular boss 102, as shown in FIG. 13. The upper knee joint means component 103 is provided with a portion having a downwardly angled, elongated opening or slot 104, which is adapted to receive the boss 102 to allow the pivotal and sliding connection required for the proper operation of the knee joint means. As shown in FIG. 16, with the boss 102 received in the opening 104 of the downwardly angled portion 105, and with the upper and lower knee joint components 103 and 100 in the leg extended position as shown in FIG. 16, the boss 102 is seated in the the upper end of the slot or opening 104 and the two cut away faces 106 and 107 of the two components 100 and 103 provide a space therebetween, through which the cable 43 passes as shown. The upper member 103 has a bore for receiving a locking pin 108 with head 109 which bears against a Belleville type spring 110. The inner end of the pin 108 is provided with a bore therethrough which receives the cable 43, so that when the cable is tensioned and the boss 102 is seated within the slot 104, the pin 108 is inwardly retracted from its dotted line position in FIG. 16 to the full line position, wherein the inner end thereof 111 seats within a recess or detent in the inner face 107 of the lower unit 100. This provides a positive locking action when the leg is in an extended position.

Figure 15:
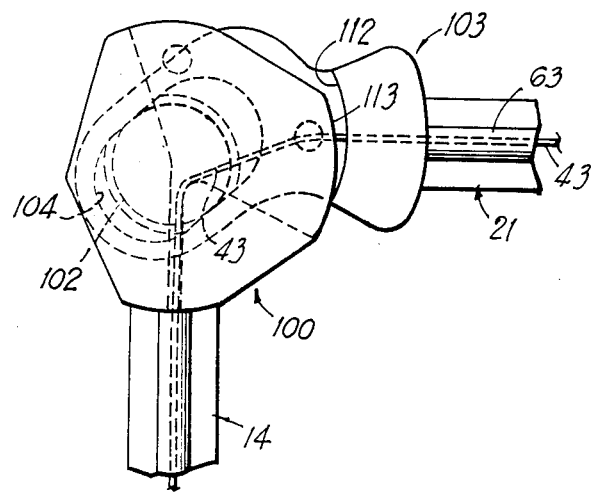
FIG. 15 is a view similar to FIG. 14 but showing the modified knee joint in flexed position.

When the tensioning means is relaxed and the pin 108 is urged by the Belleville spring 110 to the dotted line position to unlock the two components 100 and 103, the user's leg may then be flexed to a position as is shown in FIG. 15. At this time, the two cam surfaces 112 and 113 come into play so as to cause the sliding action between the two knee joint means, components 100 and 103, so that the boss 102 tends to travel towards the lower or opposite end of the opening 104.

As has been noted hereinabove, either one of the cable systems shown in FIGS. 17 and 18 may be used. It will be noted that whereas the cable 43 passing between connecting points 45 and 48, through the two springs 44 and 47, and over the guide means 51 and 50 can, when the cable 42 is completely relaxed, establish a predetermined tension in the springs 44 and 47 which cannot be lessened. That is to say, the only action which can happen through the ring or loop 52 is that the spring tension in members 44 and 47 can be equalized and increased to achieve the requisite locking or rigidifying action. In the FIG. 18 embodiment, the minimum tension in the spring 54 is not as easily controlled.

FIGS. 19 through 23 illustrate a modified knee joint means and the connecting means used to attach the elongate brace members with the knee and/or hip joint means, the ankle-foot orthosis, and the upper assembly at all points of intersection thereof. As noted hereinabove, the brace members will normally be formed of a lightweight, composite fiber/resin material, that has the further advantages of great strength and relatively reasonable cost. The composite/resin material however, can be difficult to deform once cured, and each individual using the present invention will have a unique leg configuration. For example, one individual may be slightly bow-legged while another will have a completely different leg shape.

FIG. 19 illustrates a leg brace 130 similar to the embodiment shown in FIG. 8, but capable of being modified to include upper hip joint means, as in the other embodiments. The principle here is the same, having a cable means to help rigidify the assembly; however, the knee joint means 132 is modified to a simpler, yet equally efficient construction. In order to fully exploit the modular construction, the cable connection may also be modified as shown in FIG. 19 and described below.

As shown in FIG. 20, the lower knee joint means has a V-shaped or crowned upper surface 136, the shape providing a cam surface. The sides of the lower knee joint means have recesses 138 formed therein, which are designed to receive pivot bosses 140 to provide the requisite pivoting action. Lightweight spring means 141 may be provided below the pivot bosses to aid in simulating knee action.

The upper knee joint means has a generally arcuate, V-shaped receiving surface 144, which serves as a cam follower. Both upper and lower knee joint means have a generally central channel 146 formed therein for receiving a cable means 148. The construction is such that when the cable is drawn up by the adjusting mechanism 38, and the wearer of the brace desires to straighten the leg, the knee joint means lock securely in axial alignment. The interlocking of the cam and cam follower 136 and 144 is illustrated in FIG. 22 and their shape permits mounting either in the upper position.

Cable 148 is secured near the ankle region of the ankle-foot orthosis 150. A suitable fastening means, such as turnbuckle 152 is provided to receive and secure the cable on each side of the brace. The cable extends upwardly from each connection and is looped in a manner as shown in FIG. 17 or within the ratchet mechanism 38 to equalize the tension on the cable. The ankle foot orthosis has hinge means 154 at the ankle region, the tension on the hinge being adjustable to accommodate the muscle structure of the wearer.

When the wearer of the brace desires to bend the leg, the tension on the cable is released, and the cam follower surface 144 rides the slope of the cam surface 136. This permits the movements detailed earlier and shown in FIG. 11, accommodating the compound, complex actions of the human knee.

For orthopedic applications in which the patient may require the present invention, the normal maximum angle for any particular joint is approximately fifteen to sixteen degrees, this being limited to approximately seven to eight degrees on any particular axis of the joint. Normally, angles greater than this will be corrected surgically to ensure proper functioning and to alleviate stresses and tension on the joint, ligaments and/or tendons. Thus, a five degree angle on an upper side and a five degree angle on a lower side are within the acceptable limits, the total angle being less than approximately fifteen degrees.

The preferred material used for the major components, of the present brace, i.e. the elongate side braces, the connecting arches, and such, is a composite resin, which is difficult to adjust once cured. The fiber/resin material, however, provides substantial strength with light weight, and the elongate brace members may be made in tubular form while still providing high load-bearing capacity.

With the present invention, the points of intersection between the knee and/or hip joint means, the elongate brace members and the ankle/foot orthoses, are designed to receive the connecting means designated generally by numeral 160. As shown in FIGS. 21 and 22, the connecting means are in the form of plug inserts which can be produced in molds or formed integrally with the side brace members, in a plurality of angular configurations within a range of from zero to approximately eight degrees. This may vary depending on the individual and the recommendations of the treating physician, but the range will be generally applicable to most patients not requiring corrective surgery.

FIGS. 21 and 22 show the upright tubular brace members receiving the angularly configured inserts. Each insert 160 has a first section 162, having a vertical axis parallel to the joint and, a second section 164, having a vertical axis diverging from that of the first section. The inserts also have a central channel means 166 extending axially therethrough for receiving cable 148. An epoxy 168 or similar adhesive secures the assembly together. The adhesive material can be softened with heat or other suitable processes for adjusting the modular brace as the wearer grows. A press or wedged fit may also be employed for the connecting means 160. In the alternate method of construction, section 164 is formed integrally with the brace member.

The inserts may be provided with no angle between the two sections or the axis of each section may diverge within the range of approximately zero to eight degrees to accommodate the leg shape of the particular wearer. A plurality of angular configurations are provided for the treating physician, requiring only that the physician determine the requisite angle.

The angle provided may be in any plane, an illustrative example having the first section at the apex of a cone within the specified range, and the second section extending away from the first at any position around the cone. Thus, any leg configuration may be accommodated with the present brace. The inserts may be conveniently formed in a molding process, in which the various angles are built into the mold.

An alternate construction for the inserts involves the use of a heat-yielding, thermoset plastic or similar material which can be softened upon heat application and formed to the desired angle. A similar thermoplastic material may be used for the upright brace members, as noted hereinabove, and the inserts may be formed integrally with the brace members. Thus, the end portions of the uprights would have an angularly configured section for conforming to the user's leg configuration and a straight section that is received into the knee joint, hip joint or ankle-foot orthosis. This technique is also well suited for the modular construction of the present invention.

While an embodiment of an Orthopedic Leg Brace, and modifications thereof, have been shown and described in detail herein, various additional changes and modifications may be made without departing from the scope of the present invention.

We claim:

1. A modular orthopedic leg brace assembly comprising a first pair of braces for receiving the lower portion of a user's leg therebetween, a second pair of side braces for receiving the thigh portion of a user's leg therebetween so that the side braces of the first and second pairs are generally aligned when the user's leg is straight, knee joint means connecting the proximal ends of the side braces of the first and second pairs for pivotally interconnecting said proximal ends during flexion and extension of the user's leg, said side braces and knee joint means having hollow end portions at the points of connection thereof with connecting means disposed in said hollow end portions for releasably joining said side braces and knee joint means, flexible tension means threaded through said side braces, connecting means, and respective knee joint means for interconnecting said assembly, and user manipulated means for increasing the tension in said flexible tension means and drawing said knee joint means together to form a rigid brace offset between said first and second pairs when a user's leg is extended and for decreasing the tension in said flexible tension means to allow said knee means to at least approximate the normal action of a user's knee joint when a user's leg is flexed.

2. An orthopedic leg brace assembly as defined in claim 1 including a foot orthosis joining the distal ends of said first pair of side braces with said connecting means engaging said foot orthosis and said distal ends.

3. An orthopedic leg brace assembly as defined in claim 2 in which said connecting means have two sections disposed at an angle from each other within the range of approximately zero to eight degrees.

4. An orthopedic leg brace assembly as defined in claim 1 in which said connecting means have two sections disposed at an angle from each other within the range of approximately zero to eight degrees.

5. An orthopedic leg brace assembly as defined in claim 1, including hip joint means pivotally mounted between said tensioning means and said knee joint means for at least approximating the movement of a user's hip joint when the user's leg is flexed.

6. In an orthopedic leg brace assembly as defined in claim 5 in which said hip joint means includes passage means disposed generally centrally therethrough for receiving said tension member and is designed to accept said connecting means for joining said hip joint means with said upper brace.

7. An orthopedic leg brace assembly comprising a lower side brace having securing means for firmly anchoring a said lower side brace to the side of a user's leg, an upper side brace having securing means for firmly anchoring said upper side brace to the side of a user's thigh, said upper and lower side braces having connecting means disposed in the proximal and distal ends thereof and knee joint means designed to receive said connecting means for releasably joining said braces and said knee joint means, said knee joint means pivotally and slidably joining said upper and lower braces to allow said braces and knee joint means to move toward and away from each other in at least an approximation of the normal movement of a user's knee during extension and flexion of a user's leg, passage means disposed in said upper and lower braces, said knee joint means, and said connecting means, said passage means being generally centrally disposed therein, user actuated tensioning means disposed in said passage means for drawing said knee joint means together in generally axial alignment when a user's leg is extended, and cam means in said knee joint means for moving the proximal end of said upper side brace away from the proximal end of said lower brace when a user's leg is flexed.

8. An orthopedic leg brace assembly as defined in claim 7 including a hinged ankle foot orthosis joining the distal ends of said first pair of side braces with said connecting means engaging said foot orthosis and said distal ends.

9. An orthopedic leg brace assembly as defined in claim 8 in which said connecting means have two sections disposed at an angle from each other within the range of approximately zero to eight degrees.

10. An orthopedic leg brace assembly as defined in claim 7 in which said connecting means have two sections disposed at an angle from each other within the range of approximately zero to eight degrees.

11. In an orthopedic leg brace assembly as defined in claim 7, including hip joint means pivotally mounted between said tensioning means and said knee joint means for at least approximating the movement of a user's hip joint when the user's leg is flexed.

12. In an orthopedic leg brace assembly as defined in claim 11, in which said hip joint means includes passage means disposed generally centrally therethrough for receiving said tension member and is designed to accept said connecting means for joining said hip joint means with said upper braces.

13. A modular orthopedic leg brace assembly comprising a first pair of side braces adapted to receive the lower portion of a user's leg therebetween, having securing means for firmly anchoring them to a user's leg and an ankle-foot orthosis joining the distal ends of said braces, a second pair of side braces adapted to receive the thigh portion of a user's leg therebetween and having securing means for firmly anchoring them to a user's thigh so that said first and second braces are generally aligned when the user's leg is straight, knee joint means connecting the proximal ends of the side braces of the first and second pairs and being slidably and pivotally interconnected for flexion and extension of the user's leg, connecting means disposed between said ankle-foot orthosis and said first braces and between said knee joint means and said first and second braces for releasable connection thereof, said braces, knee joint means and connecting means having central passage means therethrough, flexible tension means threaded through said passage means for aligning and drawing together said knee joint means when a user's leg is extended, and user manipulated means for increasing the tension in said flexible tension means to draw together said knee joint means and to form a rigid brace effect between said first and second pairs when a user's leg is extended and for decreasing the tension in said flexible tension means to allow said knee joint means to at least approximate the normal action of a user's knee joint when a user's leg is flexed.

14. An orthopedic leg brace assembly as defined in claim 13 including a foot orthosis joining the distal ends of said first pair of side braces with said connecting means engaging said foot orthosis and said distal ends.

15. An orthopedic leg brace assembly as defined in claim 14 in which said connecting means have two sections disposed at an angle from each other within the range of approximately zero to eight degrees.

16. An orthopedic leg brace assembly as defined in claim 15 in which said connecting means have two sections disposed at an angle from each other within the range of approximately zero to eight degrees.

17. An orthopedic leg brace assembly as defined in claim 13, and including hip joint means pivotally mounted between said tensioning means and said knee joint means for at least approximating the movement of a user's hip joint when the user's leg is flexed.

18. An orthopedic leg brace assembly as defined in claim 13 in which said knee joint means includes a cam and cam follower, and spring means for urging said cam follower along said cam.

19. An orthopedic leg brace assembly as defined in claim 13 in which said connecting means are formed integrally with said side braces and have an angularly configured section integral with said side braces and a straight section relative to said side braces and angular section for connecting said side braces with said knee joint means and said ankle-foot orthosis.

* * * * *